(12) United States Patent
Fujimoto

(10) Patent No.: US 11,045,486 B2
(45) Date of Patent: Jun. 29, 2021

(54) THERAPEUTIC METHOD AND THERAPEUTIC AGENT FOR ATOPIC DERMATITIS IN ANIMALS

(71) Applicant: Yoshihiko Fujimoto, Fukuoka (JP)

(72) Inventor: Yoshihiko Fujimoto, Fukuoka (JP)

(*) Notice: Subject to any disclaimer, the term of this patent is extended or adjusted under 35 U.S.C. 154(b) by 0 days.

(21) Appl. No.: 16/062,335

(22) PCT Filed: Oct. 25, 2016

(86) PCT No.: PCT/JP2016/081648
§ 371 (c)(1),
(2) Date: Jun. 14, 2018

(87) PCT Pub. No.: WO2017/104269
PCT Pub. Date: Jun. 22, 2017

(65) Prior Publication Data
US 2018/0369263 A1 Dec. 27, 2018

(30) Foreign Application Priority Data
Dec. 14, 2015 (JP) .............................. JP2015-243664

(51) Int. Cl.
*A61K 31/7048* (2006.01)
*A61K 31/522* (2006.01)
*A61P 17/00* (2006.01)

(52) U.S. Cl.
CPC ........ *A61K 31/7048* (2013.01); *A61K 31/522* (2013.01); *A61P 17/00* (2018.01); *A61K 2300/00* (2013.01)

(58) Field of Classification Search
CPC .......................... A61K 31/7048; A61K 31/522
See application file for complete search history.

(56) References Cited

U.S. PATENT DOCUMENTS

2009/0005326 A1* 1/2009 Murthy .............. A61K 31/7048
514/29

OTHER PUBLICATIONS

Marsella, R. et al., Veterinary Medicine: Research and Reports, "An update on the treatment of canine atopic dermatitis", 2012, vol. 3, pp. 85-91 (Year: 2012).*
McEwan, N. A. et al., Veterinary Dermatology, "A two-dimensional morphological study of corneocytes from healthy dogs and cats and from dogs with atopic dermatitis", 2009, vol. 20, No. 5-6, pp. 360-368 (Year: 2009).*
Olivry et al; Treatment of canine atopic dermatitis: 2010 clinical practice guidelines from the International Task Force on Canine Atopic Dermatitis; Veterinary Dermatology, 21, pp. 233-248; 2010.
Olivry et al; The ACVD task force on canine atopic dermatitis (XX): glucocorticoid pharmacotherapy, Veterinary Immunology and Immunopathology, 81, pp. 317-322; 2001.
Olivry et al; Evidence-based veterinary dermatology: a systematic review of the pharmacotherapy of canine atopic dermatitis; Veterinary Dermatology, 14, pp. 121-146; 2003.
Yotsumoto et al., Clinical effect of roxithromycin on purulent dermatosis, Journal of Dermatology, 56(6), pp. 1241-1245; 1994 and English abstract.
Tokura, Drugs acting on T lymphocytes for the treatment of atopic dermatitis, Japanese Journal of Inflammation,19, pp. 101-105; 1999 and English abstract.
Nakamura; Roxithromycin Suppresses Secretion of IL-13, CCL17/TARC and CCL22/MDC by Bone Marrow Derived Mast Cells and Improves Eosinophilic Pustular Folliculitis; Skin Research, 11 (Suppl.19), pp. 31-35; 2012 and English abstract.
Yukari Okubo et al., Clinical effect of roxithromycin on bacterial skin diseases associated with atopic dermatitis and its effect on neutrophil function Japanese Journal of Allergology, 44(3-2), pp. 413; 1995 and English abstract.
Scott et al; Pentoxifylline for the Management of Pruritus in Canine Atopic Dermatitis: An Open Clinical Trial with 37 Dogs; Jpn J Veterinary Dermatology, 13(1), pp. 5-11; 2007.
Espinosa et al; Phosphodiesterase Inhibitors as Immunomodulatory Drugs; Immunologia, 22(1), pp. 39-52; 2003.
Singh et al., Therapeutic management of canine dermatitis by combination of pentoxifylline and PUFAs, J.Vet.Pharmacol. Therap., 33, pp. 495-498; 2010.
Shimizu, Textbook of modern dermatology, 1st edition, pp. 93-95, Nakayama Shoten Co., Ltd., Tokyo; 2011 and English Abstract.
Marsella et al; Double-blinded cross-over study on the efficacy of pentoxifylline for canine atopy; Veterinary Dermatology, 11, pp. 255-260; 2000.
Plant et al; Development and Validation of the Canine Atopic Dermatitis Lesion Index, a scale for the rapid scoring of lesion severity in canine atopic dermatitis; Veterinary Dermatology, 23, pp. 515-e103; 2012.
Favrot et al; A prospective study on the clinical features of chronic canine atopic dermatitis and its diagnosis; Veterinary Dermatology. 21: pp. 23-30; 2010.
Hand et al; Influence of Pentoxifylline and Its Derivatives on Antibiotic Uptake and Superoxide Generation by Human Phagocytic Cells; Antimicrobial Agents Chemotherapy, 1995, vol. 39 No. 7, pp. 1574-1579.
Adachi et al; The effect of antibiotics on the production of superantigen from *Staphylococcus aureus* isolated from atopic dermatitis; J. Dermatological Science., 2002, vol. 28, pp. 76-83.

(Continued)

*Primary Examiner* — Bahar Craigo
(74) *Attorney, Agent, or Firm* — Renner, Otto, Boisselle & Sklar, LLP

(57) ABSTRACT

Provided are a therapeutic agent and a therapeutic method for canine atopic dermatitis. The therapeutic method for atopic dermatitis in animals and the therapeutic drug for atopic dermatitis in animals are characterized in that 2.5-10.0 mg/kg of roxithromycin and/or a pharmaceutically acceptable salt thereof and 12.5-50.0 mg/kg of pentoxifylline and/or a pharmaceutically acceptable salt thereof are to be simultaneously administered along with meals at 12-hour intervals for 60 days. The present invention provides an advantageous effect of preventing recurrence of symptoms for at least 30 days even after cessation of drug administration.

4 Claims, 1 Drawing Sheet

(56) References Cited

OTHER PUBLICATIONS

Olivry et al; Validation of the Canine Atopic Dermatitis Extent and Severity Index (CADESI)-4, a simplified severity scale for assessing skin lesions of atopic dermatitis in dogs; Veterinary Dermatology 2014, 25: pp. 77-e25.
Olivry et al; Validation of CADESI-03, a severity scale for clinical trials enrolling dogs with atopic dermatitis; Jpn J Veterinary Dermatology, Jun. 2008; pp. 63-72.
Favrot, Clinical signs and diagnosis of canine atopic dermatitis; EJCAP—vol. 19—Issue Dec. 3 pp. 219-222; 2009.
International Search Report for related PCT/JP2016/081648 dated Nov. 28, 2016.

\* cited by examiner

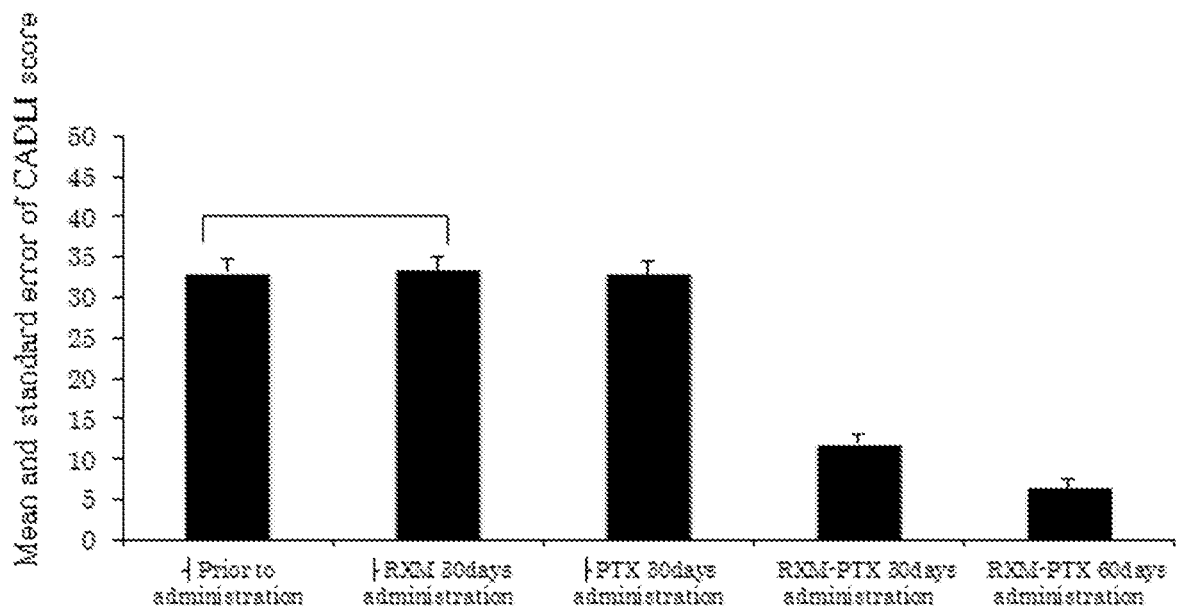
Figure 1. Comparison of CADLI score after each drug administration
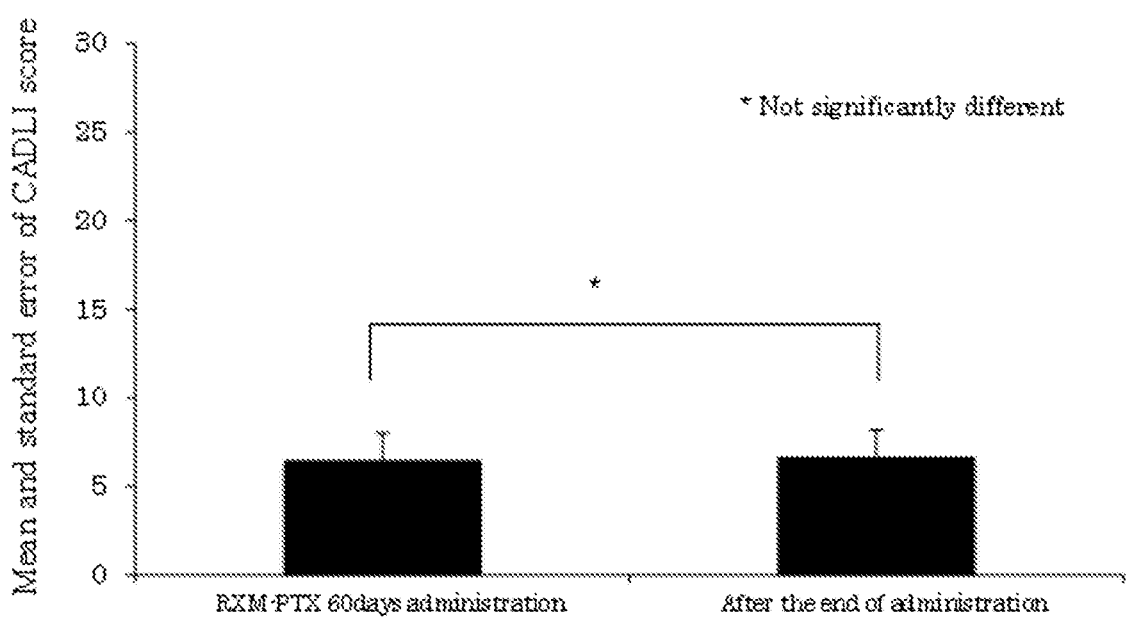
Figure 2. Comparison of CADLI score before and after the end of administration

THERAPEUTIC METHOD AND THERAPEUTIC AGENT FOR ATOPIC DERMATITIS IN ANIMALS

TECHNICAL FIELD

This invention relates treatment method and treating agent for animal atopic dermatitis. More specifically, it relates to treatment method and treating agent for dog atopic dermatitis.

BACKGROUND ART

There is steroid treatment as general method for treatment of canine atopic dermatitis (CAD). Although this treatment has an effect of reducing itching (non-patent literature), side effects occur if it is used for long-term continuously (non-patent literature 2 and 3).

As treatment of canine atopic dermatitis in the clinical setting, Steroid therapy, non-steroid therapy, cyclosporin therapy, hyposensitization therapy, interferon gamma therapy, fatty acid therapy, diet therapy, etc. are listed. However, at present, Treatment other than steroids can not ameliorate canine atopic dermatitis with a therapeutic effect equal to or higher than that of steroid therapy.

In reality, in clinical practice, therapy that relied on steroids is still mainstream (non-patent literature 1). However, as soon as medication is finished, its steroid therapy also causes recurrence of symptoms (non-patent literatures 2 and 3). Repetition of remission and relapse often results in gradual increase in drug dosage until symptomatic remission is obtained, and concern of side effects increases.

Roxithromycin (RXM) is one of 14-membered ring macrolide antibiotics, and human is expected to suppress staphylococcal induced superantigen presenting ability by epidermal immunomodulation effect, and are used for secondary infection control of acne and psoriasis of human (Non-Patent literature 4). It is known that in addition to the action as an antibiotic, RXM suppresses the antigen presenting ability of Langerhans cells, decreases the production of IL-1β, and that by suppressing IFN-γ induced MHC class II inhibits cytokine production such as IL-1a (Non-Patent literature 5). Recently, it has also been confirmed that it has a function of suppressing the secretion of IL-13 secreted from bone marrow-derived mast cell which is a precursor of mast cell showing an important role in canine atopic dermatitis, CCL 17 and CCL 22 which is one of CC chemokines (Non-Patent literature 6). However, there was no report that improvement of clinical symptoms of atopic dermatitis in dogs was observed with administration of roxithromycin alone, and it is used for chronic recurrent staphylococcal pyoderma associated with epidermal microcyclics in the present (Non-Patent literature 7).

Pentoxifylline (PTX), on the other hand, is a synthetic xanthine derivative and is a nonselective phosphodiesterase inhibitor. Its pharmacological action suppresses leukocyte adhesion to keratinocytes and endothelial cells and has the action of decreasing neutrophil degranulation and active oxygen release (Non-Patent literature 8). In addition, it has an action of rescuing cytokines such as interleukin (IL)-1, IL-2, IL-4, IL-6, IL-8, IL-10, IL-12, tumor necrosis factor (TNF-alpha) and Interferon (IFN)-gamma etc. (Non-Patent literature 8). By these actions, pentoxifylline is effective for contact allergy, vasculitis, and other immune-mediated diseases (Non-Patent Document 9), and In particular, it has been said that it has an effect of reducing the dosage of glucocorticoid (Non-Patent Document 8). A few clinical symptoms showing significant effect has been known for some time when single dose of pentoxifylline alone was administered to dogs exhibiting canine atopic dermatitis. D. W. Scott et al. reported that it is effective in 7 out of 37 patients (19%) by single administration of pentoxifylline (Non-Patent Document 8), S. K. Singh and colleagues reported that clinical symptoms showing effect are existed when administered for 60 days continuously in clinical symptoms showing canine atopic dermatitis symptoms of extremely minor (almost systemic symptoms can not be confirmed) of 30 to 39 points with CADESI-02 whose highest point is 360 as an index (Non-Patent Document 10). In addition, R. Marsella et al reported that improvement of lesions and itching was observed only in an erythematosus lesion (Non-Patent Document 11) which is an acute or subacute lesion (Non-Patent Document 12). However, currently, there is no report that dramatically improved severe canine atopic dermatitis accompanied by lichenification, which is a chronic recurrent inflammatory lesion (severe so that side effects due to repeated dosing of steroid drugs are of concern) by administration of pentoxifylline alone. As mentioned above, although administration of pentoxifylline alone can suppress acute or subacute inflammation (that is, CADESI is a minor one-time type of dermatitis of about 30 to 50), It has no effect on severe recurrent dermatitis with lichenification, which is problematic every day in the clinical setting (side effects caused by repeated dosing of steroid drugs must be concerned). In other words, it can be said that acute or subacute dermatitis can be sufficiently curable with steroid drugs, and dare to use pentoxifylline is costly and has side effects, so it can be said that merit is small. Therefore, as the common sense of the world, it is said that "should not be used as the first therapeutic agent in canine atopic dermatitis" (Non-Patent Document 13), at the present time, it is used only as a supplementary aid for therapeutic drugs such as steroid drugs and cyclosporin drugs (Non-Patent Document 8).

Therefore, there has been a need for a therapeutic agent and a treatment method for atopic dermatitis which replaces a steroid agent and treatment method.

RELATED ART DOCUMENTS

Non-Patent Documents

Non-patent literature 1: Olivry T, DeBoer D J, Favrot C, Jackson H A, Mueller R S, Nuttall T, et al: Treatment of canine atopic dermatitis: 2010 clinical practice guidelines from the International Task Force on Canine Atopic Dermatitis. Vet Dermatol, 21, 233-248 (2010)

Non-patent literature 2: Olivry T, Sousa C A: The ACVD task force on canine atopic dermatitis (XX): glucocorticoid pharmacotherapy. Vet Immunol Immunopathol, 81, 317-322 (2001)

Non-patent literature 3: Olivry T, Mueller R S, and the international task force on canine atopic dermatitis: Evidence-based veterinary dermatology: a systematic review of the pharmacotherapy of canine atopic dermatitis. Vet Dermatol, 14, 121-146 (2003)

Non-patent literature 4: Shinichi Yotsumoto, Mitsuru Setoyama, Tamotsu Kanzaki, Masaaki Tashiro: Clinical effect of roxythromycine on purulent dermatosis. The Nishinihon Journal of Dermatology, 56 (6), 1241-1245 (1994).

Non-patent literature 5: A. Tokura: Agent for treatment for atopic dermatitis that acts on T lymphocytes. Januray j. Inflammation, 19, 101-105 (1999)

Non-patent literature 6: M. Nakamura: Roxithromycin Suppresses Secretion of IL-13, CCL17/TARC and CCL22/MDC by Bone Marrow Derived Mast Cells and Improves Eosinophilic Pustular Folliculitis. Skin Research, 11 (Suppl. 19), 31-35 (2012)

Non-patent literature 7: Yukari Okubo, Yasuaki Tokuda, Yoshiro Sakazaki, Masaomi Yamashiro: Clinical effect of roxithromycin on bacterial skin diseases associated with atopic dermatitis and its effect on neutrophil function. Japanese Journal of Allergology, 44 (3-2), 413 (1995)

Non-patent literature 8: Danny W Scott, William H Miller: Pentoxifyline for the Management of Pruritus in Canine Atopic Dermatitis: An Open Clinical Trial With 37 Dogs. Jpn J Vet Dermatol, 13(1), 5-11 (2007)

Non-patent literature 9: E Layseca, F Sanchez, R Gonzalez: Phosphodiesterase Inhibitors as Immunomodulatory Drugs. Immunologia, 22(1), 39-52 (2003)

Non-patent literature 10: S. K. Singh, et al: Therapeutic management of canine atopic dermatitis by combination of pentoxifylline and PUFAs. J. Vet. Pharmacol. Therap., 33, 495-498 (2010)

Non-patent literature 11: Hiroshi Shimizu, Textbook of modern dermatology, 1st edition, p 93-95, Nakayama Shoten Co., Ltd., Tokyo (2011)

Non-patent literature 12: R. MARSELLA, et al: Double-blinded cross-over study on the efficacy of pentoxifylline for canine atopy. Vet Dermatology, 11, 255-260 (2000)

Non-patent literature 13: Veterinary Dermatology, 21, p 233-248 (2010), 2011, Corrected on June, 28th.

Non-patent literature 14: Jon D. Plant, Kinga Gortel, Marcel Kovalik, Nayak L. Polissar. et al: Development and validation of the Canine Atopic Dermatitis Lesion Index, a scale for the rapid scoring of lesion severity in canine atopic dermatitis. Vet Dermatol, 23, 515-e103 (2012)

Non-patent literature 15: Favrot C, Steffan J, Seewald W, et al. A prospective study on the clinical features of chronic canine atopic dermatitis and its diagnosis. Vet Dermatol. 21: 23-30. 2010.

SUMMARY OF THE INVENTION

Problem to be Solved by the Invention

The present invention was made to address the above-described problems, and it is an object thereof to provide novel therapeutic methods and therapeutic agents for atopic dermatitis in dogs are provided.

Means for Solving the Problem

The inventors compared changes in clinical symptoms caused by administration of roxithromycin alone, administration of pentoxifylline alone, administration of roxithromycin/pentoxifylline in combination using the CADLI index (Non-Patent Document 14), found out the usefulness of treatment with roxithromycin and pentoxifylline in combination and completed the invention.

(1) A method for treating atopic dermatitis in an animal according to (1), comprising administering roxithromycin and pentoxifylline in combination. In the present specification, the animal may be an animal that does not include humans (excluding humans).

(2) The method for treating atopic dermatitis according to (1), wherein the animal is a dog.

(3) A method for treating atopic dermatitis in an animal according to (1) or (2), characterized by administrating 2.5 mg/kg to 10 mg/kg of roxithromycin and 12.5 mg/kg to 50.0 mg/kg of pentoxifylline at the same time with meals for 12 hours at 60 hours for 60 days.

(4) The method for treating atopic dermatitis according to claim 2 or 3, wherein the dog is a dog whose sum of the SQK values is larger than the sum of the SLK values. At this point, the dog may be a dog whose SQK appearance area is larger than the appearance area of SLK. Preferably, the dog is a dog with the sum of the SQK values of the five sites (e.g. under the neck, the fossa, the back, the forearm, the lower leg) are greater than the sum of the SLK values. These are the same in the followings.

(5) A therapeutic agent for atopic dermatitis for animals comprising roxithromycin and pentoxifylline.

(6) A therapeutic agent for atopic dermatitis for animals according to (5), wherein a said animal is a dog.

(7) A therapeutic agent for atopic dermatitis for animals according to (5) or (6), characterized by administrating roxithromycin at 2.5 mg/kg to 10 mg/kg and pentoxifylline at 12.5 mg/kg to 50.0 mg/kg at the same time with meals every 12 hours for 60 days.

(8) A therapeutic agent for atopic dermatitis for animals according to (6) or (7), wherein the said dog is a dog whose sum of SQK values are greater than the sum of SLK values.

(9) Method for treating atopic dermatitis in animals, characterized by administrating roxithromycin and/or a pharmaceutically acceptable salt thereof and pentoxifylline and/or a pharmaceutically acceptable salt thereof in combination.

(10) Method for treating atopic dermatitis according to (9), wherein the said animal is a dog.

(11) Method for treating atopic dermatitis according to (9) or (10), characterized by administrating 2.5 mg/kg to 10 mg/kg of roxithromycin and/or a pharmaceutically acceptable salt thereof, 12.5 mg/kg to 50.0 mg/kg of pentoxifylline and/or a pharmaceutically acceptable salt thereof together with meals at the same time for 60 days every 12 hours

(12) Method for treating atopic dermatitis according to (9) or (10), wherein the said dog is a dog whose sum of SQK values is greater than the sum of SLK values.

(13) A therapeutic agent for atopic dermatitis for animals including roxithromycin and/or a pharmaceutically acceptable salt thereof and pentoxifylline and/or a pharmaceutically acceptable salt thereof.

(14) A therapeutic agent for atopic dermatitis for animals according to (13), wherein the said animal is a dog.

(15) A therapeutic agent for atopic dermatitis for animals according to (13) or (14), characterized by administrating 2.5 mg/kg to 10 mg/kg of roxithromycin and/or a pharmaceutically acceptable salt thereof, and 12.5 mg/kg to 50.0 mg/kg of pentoxifylline and/or a pharmaceutically acceptable salt thereof together with meals at the same time for 60 days every 12 hours.

(16) A therapeutic agent for atopic dermatitis for animals according to (14) or (15), characterized by that the said dog is a dog whose sum of SQK values is greater than the sum of SLK values.

Effects of the Invention

According to the present invention, canine atopic dermatitis can be treated.

BRIEF DESCRIPTION OF DRAWINGS

FIG. 1 is a graph showing a comparison of CADLI scores after drug administration.

FIG. 2 is a graph showing CADLI scores after dosing is completed.

DESCRIPTION OF EMBODIMENTS

In the present invention, roxithromycin and pentoxifylline are administered together with a meal at the same time. By simultaneously administering, treatment effect of atopic dermatitis which can not be seen with single agent administration of each drug is obtained. Here, "at the same time" does not necessarily mean exactly the same time but means that both are administered, for example, within 30 minutes, more preferably within 20 minutes, further preferably within 10 minutes. In addition, "with meal" means that it may be administered with a meal at the time of meal, and it may be administered within 1 hour after the meal, more preferably within 30 minutes, further preferably within 20 minutes.

As a form of simultaneous administration, separate drugs may be administered at the same time, or a mixed drug may be prepared from the beginning and administered.

It is preferable to simultaneously administer roxithromycin at 5 mg/kg and pentoxifylline at 25 mg/kg at the same time with meals or after meals every 12 hours for 60 days. The dose is 2.5 mg/kg to 10 mg/kg in the case of roxithromycin, the lower limit is, more preferably 3.0 mg/kg or more, still more preferably 4.0 mg/kg or more, still more preferably 4.5 mg/kg or more, most preferably 5.0 mg/kg, and the upper limit is more preferably 8.0 mg/kg or less, further preferably 7.0 mg/kg or less, particularly preferably 6.0 mg/kg or less, Most preferably 5.0 mg/kg. In the case of pentoxifylline, the preferred dosage is 12.5 mg/kg to 50 mg/kg, more preferably the lower limit is 15.0 mg/kg or more, more preferably 17.5 mg/kg or more, Even more preferably 20.0 mg/kg or more, particularly preferably 23 mg/kg or more, most preferably 25 mg/kg, and the upper limit is more preferably 45.0 mg/kg or less, further preferably 40 mg/kg or less, Still more preferably 35.0 mg/kg or less, particularly preferably 30.0 mg/kg or less, most preferably 25 mg/kg. For these preferable upper limit and lower limit, any combination can be made for each drug. This is because atopy is almost completely cured, and even if drug administration is stopped thereafter, it will not return.

According to the present invention, by simultaneously administering roxithromycin and pentoxifylline, which did not show any effect on atopic dermatitis in dogs when administered alone respectively, the CADLI value was significantly lowered, and It has become apparent that the clinical symptoms were also dramatically improved proportionally to it.

Roxithromycin (formula I) used this time is a 14-membered ring macrolide antibiotic, but other macrolide antibiotics include erythromycin and clarithromycin etc. As long as it has the same therapeutic effect on atopic dermatitis as roxithromycin, other macrolide antibiotics and pentoxifylline may be administered in combination. Epidermal immunity regulating action and inflammatory response regulating action is expected for roxithromycin (Non-Patent Document 4), in the human body, it is used for secondary management of acne and psoriasis, chronic sinusitis, chronic respiratory tract inflammation (Non-Patent Document 4).

[Chemical formula I]

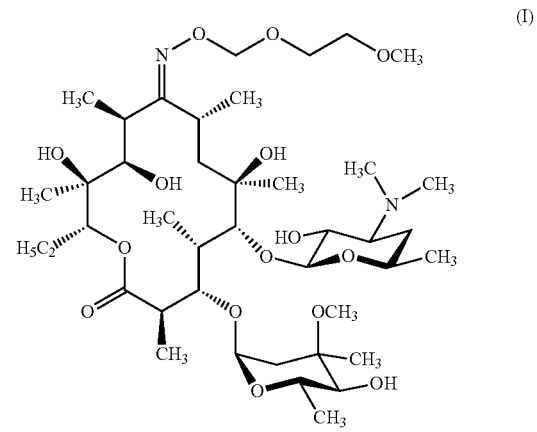

However, there was no report that it was effective against atopic dermatitis in dogs, and in this experiment as well, the aggregation index after single administration of roxithromycin was average±standard error 33.64±1.51 (CADLI aggregation index before administration Is 33.17±1.50), neither significant reduction (P=0.643, FIG. 1) nor improvement in clinical symptoms could be confirmed. That is, administration of roxithromycin alone did not seem to have sufficient therapeutic effect to improve atopic dermatitis in dogs.

Pentoxifylline (Formula II) is a synthetic xanthine derivative and is a nonselective phosphodiesterase inhibitor. Phosphodiesterase inhibitors have anti-inflammatory action (vascular endothelial protective action) by increasing intracellular cAMP concentration and cGMP concentration.

[Chemical formula II]

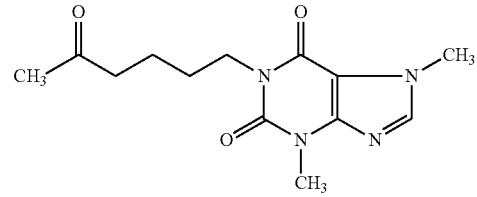

By this action, it is considered to be effective against contact allergy, vasculitis, and other immune-mediated diseases, and in particular, the effect of reducing the dosage of glucocorticoid has been shown (Non-Patent Document 8). However, there is no report that administration of pentoxifylline alone has dramatically improved the clinical symptoms of dog's atopic dermatitis with a high probability, and at the present time it has been used only as a reducing drug aid for drugs such as steroids and cyclosporin drugs (Non-Patent Document 8). In this experiment as well, the aggregation index after pentoxifylline administration was 33.09±1.52 (CADLI aggregation index before administration was 33.17±1.50) and did not show a significant decrease (P=0.983, FIG. 1), most of the clinical symptoms did not show improvement. In other words, administration of pentoxifylline alone is considered to have no therapeutic effect to improve atopic dermatitis in dogs.

Meanwhile, roxithromycin and pentoxifylline, which were not effective in each single agent administration, were administered at the same time, so that by mutual interaction, 33.17±1.50 of CALDI index before treatment were significantly decreased to 12.04±1.12 (P<0.001, FIG. 1) at 30th day, 6.51±0.97 (P<0.001, FIG. 1) at 60th day by simultaneous administration of roxithromycin-pentoxifylline, and the CALDI index was confirmed to be significantly decreased. The clinical symptoms also improved markedly to be proportional to the decrease of the CADLI index and confirmed many effects that the symptoms of canine atopic dermatitis almost disappeared. There was no difference among the breed type (Table 3), sex (Table 4) and age (Table 5), and the clinical symptoms improved in the same way. These results showed that this roxithromycin and pentoxifylline combination therapy is an effective treatment equivalent to steroid therapy for the treatment of canine atopic dermatitis.

In addition to this, the greatest advantage of this treatment is that it overcomes the problem of "recurring symptoms soon after medication is finished" which is a disadvantage of steroid therapy. In other words, if administration of drugs is stopped for 1 month with steroid therapy, the symptoms often reignite in the clinical setting. However, with this combination of roxithromycin and pentoxifylline in combination therapy, even after 30 days from stopping administration of drugs, the CADLI index was 6.68±1.01 (Table 2) and no significant increase was observed as compared with that before stopping administration of drug (P=0.817) (FIG. 2), revealed that there was no relapse of symptoms of dogs atopic dermatitis for a minimum of 30 days.

The CADLI index used in the present specification is an index representing the skin condition of atopic dermatitis, and the skin condition of the five parts of the body is scored by estimating erythema, scratch, erosion, alopecia, lichenification, hyperpigmentation (Non-Patent Document 14). Therefore, the highest point is 50 points, and closer to 50 points the skin inflammation is becoming more severe. In the case used in the present specification, the numerical value before treatment is 33.17±1.50, indicating that the symptoms of dermatitis are highly severe. If replaced to CADESI-02 used in the literature of S. K. Singh, the case of the present specification exhibits severe atopic dermatitis which shows about 238 points. This figure decreased to 12.04±1.11 after 30 days of dosing and 6.51±1.51 after 60 days, and it was remarkable for all 127 cases (100%). To be able to obtain remission of symptoms with high probability. And if medication is discontinued, there is no relapse of the symptoms for 30 days. In these two points, it was revealed that the combination therapy of roxithromycin and pentoxifylline is useful as a treatment for dog atopic dermatitis rather than steroid therapy.

As a side effects, several cases showing the symptoms of vomiting were observed throughout the whole period, but symptoms almost disappeared by encouraging owner thoroughly to make dogs to drink after meals. Biochemical tests were also conducted in all cases after drug administration was completed. In rare cases, a slight elevation of alkaline phosphatase (ALP) was observed, but there was no noticeable change other than that.

In addition, the agent for treating atopic dermatitis of dog can optionally contain other ingredients in addition to roxithromycin and pentoxifylline. The ingredients added to the medicine are determined mainly depending on the mode of administration of the medicine. When the medicine is used as a solid, for example, a filler such as lactose, a binding agent such as carboxymethylcellulose, gelatin and the like, a coloring agent, a coating agent and the like can be used, and such an agent is suitable for oral administration. It is also possible to apply it to the affected part as an external medicine in the form of cream, milky lotion, lotion, etc. by adding, for example, white petrolatum, cellulose derivative, surfactant, polyethylene glycol, silicone, olive oil or the like as a carrier or activator. When the medicine is administered as a liquid, it may contain physiologically acceptable solvents and emulsifiers and stabilizers, which are usually performed. Examples of the solvents include water, PBS, and isotonic saline. Examples of the emulsifier include polyoxyethylene based surfactants, fatty acid based surfactants, silicone and the like. Examples of the stabilizer include dog serum albumin, a polyol such as gelatin, or a saccharide such as sorbitol, trehalose and the like. The method for administering the therapeutic agent for atopic dermatitis of the present invention is not particularly limited, but the most therapeutic effect can be expected by oral administration.

If a pharmacologically acceptable salt is present in roxithromycin, a pharmacologically acceptable salt may be administered in place of roxithromycin or simultaneously with roxithromycin. That is, when used in combination with pentoxifylline, either pentoxifylline and roxithromycin, or pentoxifylline and pharmaceutically acceptable salts of roxithromycin may be administered in any combination. The pharmaceutically acceptable salt type is not particularly limited as long as it does not significantly inhibit the drug efficacy and there is no side effect, but examples thereof include a sodium salt and a calcium salt.

If a pharmaceutically acceptable salt is present in pentoxifylline, a pharmaceutically acceptable salt may be administered instead of or in combination with pentoxifylline. In this case, as a combination when administered in combination with roxithromycin, there may be four combinations: roxithromycin and pentoxifylline, pharmaceutically acceptable salt of roxithromycin and pentoxifylline, roxithromycin and pharmaceutically acceptable salt of pentoxifylline, a pharmaceutically acceptable salt of roxithromycin and a pharmaceutically acceptable salt of pentoxifylline. The pharmaceutically acceptable salt is not particularly limited as long as it does not greatly inhibit the drug efficacy and the side effect is not strong but examples thereof include a sodium salt and a calcium salt.

As well, the combination therapy of the present invention is more suitable for a dog with a large appearance area of peeled keratinocytes called Square Peeled Off Keratinocytes (SQK) showing a rectangular shape than a dog with a large appearance area of exfoliative corneocytes called a Slender Peeled off Keratinocytes (SLK) showing elongated shape.

About the appearance area of SQK and SLK, for example, it can be obtained by collecting exfoliative corneocytes from the neck, elbow, back, forearm, lower leg, etc. by tape stripping, taking a photograph under a microscope and processing the image.

A typical clinical symptom of a group that frequently has SQK is that hair coat and skin are sticky and fat that lichenified lesions are found under the neck, cubital fossa, underarm, lower abdomen and tarsus fossa.

Symptoms of cases with frequent SQK by combination administration of pentoxifylline and roxithromycin were dramatically improved. Before dosing, skin coat which had been sticky only for a long time, almost no stickiness was caused by administration of these medicines. Since the stickiness of the skin coat is the hypersecretion of the skin surface lipid itself, it is presumed that these agents also have the function of suppressing and normalizing the superficial secretion of the skin surface lipid. It is thought that these actions did not cause recurrence of symptoms of canine atopic dermatitis even when medication was discontinued.

EXAMPLES

Changes in clinical symptoms caused by administration of roxithromycin alone, administration of pentoxifylline alone, administration of roxithromycin and pentoxifylline in combination were compared using the Canine Atopic Dermatitis Lesion Index (CADLI) index, and we examined the usefulness of treatment with roxithromycin and pentoxifylline in combination.

Materials and Methods

Target animals: For five years from 2010 to 2015, at Gotofu Animal Hospital (1-1-3, Fujisaki, Sawara-ku, Fukuoka City, Fukuoka Prefecture), among dogs diagnosed as atopic dermatitis of dogs by diagnostic criteria announced by Dr. Favrot in 2010 (non patent literature 15), the examinations were conducted for 127 dogs for which the consent and cooperation of treatment were obtained from the family and whose sum of SQK were larger than the sum of SLK of the 5 parts, whose SLK and SQK value were calculated for 5 parts of the neck, the fossa, the back, the forearm, and the lower leg. As content of implementation items, in all 127 cases, roxithromycin was administered as a single agent for 30 days, and pentoxifylline was administered as a single agent for the next 30 days. During the last 60 days, roxithromycin and pentoxifylline were administered in combination. The constituent of the targeted dog type is as shown in (Table 1). The constituent of the gender was 57 males (35 castrated with 35 male), 70 females (35 contraceptives already) (Table 1).

TABLE 1

Breed and sex data on 127 dogs with atopic dermatitis

| Breed | male | castrated male | female | spayed female |
|---|---|---|---|---|
| Shih Tzu | 4 | 9 | 12 | 6 |
| Shiba | 4 | 3 | 3 | 5 |
| Miniature dachshund | 3 | 3 | 4 | 4 |
| Toy Poodle | 4 | 4 | 4 | 2 |
| Yorkshire Terrier | 0 | 2 | 2 | 3 |
| Mongrel | 0 | 2 | 1 | 4 |
| Chihuahua | 0 | 3 | 2 | 1 |
| West Highland white terrier | 1 | 0 | 2 | 2 |
| Pug | 1 | 0 | 1 | 3 |
| Welsh Corgi | 2 | 2 | 0 | 0 |
| French Bulldog | 1 | 2 | 1 | 0 |
| Golden retriever | 1 | 2 | 1 | 0 |
| Cavalier Charles Spaniel | 0 | 0 | 1 | 1 |
| Beagle | 0 | 1 | 1 | 0 |
| Pomeranian | 0 | 1 | 0 | 1 |
| Border Collie | 0 | 0 | 0 | 1 |
| Pekingese | 1 | 0 | 0 | 0 |
| Wire Fox Terrier | 0 | 1 | 0 | 0 |
| Lhasa apso | 0 | 0 | 0 | 1 |
| Miniature schnauzer | 0 | 0 | 0 | 1 |

The age constituent at the time of examination was from 2 years old to 18 years old, and the average was 7.8 years old. For individuals to be treated, individuals that met Dr. Favrot's diagnostic criteria were selected. However, even individuals meeting the diagnostic criteria of Dr. Favrot, those individuals who had infectious skin diseases of ectoparasites were not included in this study.

Methods: In all 127 cases, 5 mg/kg of roxithromycin alone was orally administered with meals every 12 hours for the first 30 days. For the next 30 days, pentoxifylline alone was orally administered at 25 mg/kg with meals every 12 hours. For the next 60 days, 5 mg/kg of roxithromycin and 25 mg/kg of pentoxifylline were orally administered simultaneously with meals every 12 hours. After that, administration of roxithromycin and pentoxifylline was discontinued and a follow-up study was conducted for 30 days. For all treatment periods, meals were allowed to feed freely without restriction. Also, shampoo was carried out at home once a week. Local corticosteroid therapy was performed at any time as long as there was a strong itching lesion Estimation Methods:

After measurement, roxithromycin (RXM) was administered as a single agent for 30 days. After administration, CADLI index was measured to ascertain the skin condition, and it was judged whether roxithromycin has the ability to improve atopic dermatitis by comparing the change of numerical values before and after medication. Similarly, for pentoxifylline (PTX), it was estimated whether pentoxifylline has the effect of improving canine atopic dermatitis by measuring the CADLI index as an index and comparing the values before and after administration. Finally, for administration of roxithromycin and pentoxifylline in combination, the CADLI index was measured on the 30th and 60th days of administration, respectively, and the effect of the drug was evaluated by comparing the values.

(Results)

In all 127 cases, CADLI index was measured to ascertain the status of atopic dermatitis in dogs before starting medication. The mean±standard error of that number was 33.17±1.50 (Table 2).

TABLE 2

The average value and standard error of CADI score of data on 127 dogs

|  | Prior to administration | RXM 30-days administration | PTX 30-days administration | RXM*PTX 30-days administration | RXM*PTX 60-days administration | After the end of administration |
|---|---|---|---|---|---|---|
| Average value | 33.17 | 33.64 | 33.09 | 12.04 | 6.51 | 6.68 |
| Standard error | 1.35 | 1.51 | 1.52 | 1.12 | 0.97 | 1.01 |

The CADLI index after administration of roxithromycin alone was 33.64±1.51 (Table 2), and as compared with 33.17±1.50 before the start of dosing, there was no significant decrease in the CADLI index due to administration of roxithromycin (P=0.643) (FIG. 1), there was no effect of improving canine atopic dermatitis. Similarly, there was no significant decrease (P=0.983) (FIG. 1), in pentoxifylline monotherapy compared to 33.09±1.52 (Table 2) and 33.17±1.50 prior to the start of dosing and was also unable to confirm the effect of improving the symptoms of atopic dermatitis in dogs. On the other hand, administration of roxithromycin and pentoxifylline in combination resulted in a CADLI index of 12.04±1.12 (Table 2) (P<0.001) on Day 30 and 6.51±0.97 (Table 2) (P<0.001) on Day 60 There was a clear decrease in the number compared to 33.17±1.50 before the start of dosing (FIG. 1).

The symptoms of clinical symptoms were remarkably improved such that dogs had more remarkable improvement in atopic dermatitis, such as being more improved on Day 60 than Day 30, as being proportional to the decrease in these values. As the skin condition improved remarkably, roxithromycin and pentoxifylline administration in combination was terminated and after completion the symptoms of dogs' atopic dermatitis were checked for recurrence.

The CADLI index after 30 days of administration of roxithromycin and pentoxifylline was 6.68±1.01 (Table 2) and did not increase significantly as compared with the numerical value 6.51±0.97 before the administration of roxithromycin pentoxifylline P=0.817) (FIG. 2), no deterioration of clinical symptoms could be confirmed. In other words, even when administration of roxithromycin and pentoxifylline was discontinued, it became clear that there was no relapse of the symptoms for 30 days.

The effect of decreasing CADLI index did not differ according to breed (Table 3), gender (Table 4), age (Table 5), and clinical symptoms improved in the same way. Therefore, it was found that the combined administration of the present invention is effective regardless of breed, sex, and age.

TABLE 3

The average value and standard error of CADLI score of data on each dog breeds

| Breed | Prior to administration | RXM 30-days administration | PTX 30-days administration | RXM*PTX 30-days administration | RXM*PTX 60-days administration | After the end of administration |
|---|---|---|---|---|---|---|
| Shih Tzu | 32.78 ± 2.90 | 33.39 ± 2.88 | 32.94 ± 3.09 | 11.42 ± 2.15 | 4.68 ± 1.52 | 4.74 ± 1.54 |
| Shiba | 35.13 ± 4.55 | 35.60 ± 4.44 | 34.93 ± 4.45 | 12.20 ± 3.34 | 8.40 ± 4.09 | 8.67 ± 4.30 |
| Miniature dachschund | 28.79 ± 4.16 | 29.00 ± 4.24 | 28.64 ± 4.11 | 10.86 ± 4.06 | 5.86 ± 2.75 | 5.86 ± 2.75 |
| Toy Poodle | 37.14 ± 5.58 | 37.57 ± 5.51 | 36.86 ± 5.42 | 12.79 ± 4.13 | 6.21 ± 2.95 | 6.28 ± 3.04 |
| Yorkshire Terrier | 22.57 ± 8.21 | 23.00 ± 8.56 | 22.29 ± 7.94 | 7.29 ± 3.45 | 3.29 ± 2.78 | 3.57 ± 2.75 |
| Mongrel | 36.00 ± 6.08 | 36.57 ± 6.25 | 36.00 ± 6.08 | 13.71 ± 3.09 | 6.57 ± 5.81 | 6.86 ± 6.12 |
| Chihuahua | 31.33 ± 9.02 | 31.67 ± 9.18 | 31.00 ± 9.01 | 16.67 ± 6.23 | 9.00 ± 7.59 | 9.50 ± 7.89 |
| West Highland white terrier | 34.40 ± 7.91 | 35.00 ± 8.08 | 34.40 ± 7.91 | 13.40 ± 3.90 | 6.40 ± 1.70 | 6.60 ± 2.10 |
| Pug | 35.80 ± 3.37 | 35.30 ± 3.63 | 35.60 ± 3.48 | 11.20 ± 7.38 | 7.00 ± 5.66 | 7.00 ± 5.66 |
| Welsh Corgi | 31.50 ± 6.11 | 31.50 ± 6.98 | 31.50 ± 6.11 | 9.00 ± 7.80 | 4.75 ± 2.61 | 4.75 ± 2.61 |
| Others | 35.37 ± 3.67 | 36.16 ± 3.50 | 35.26 ± 3.66 | 13.42 ± 3.36 | 9.37 ± 2.74 | 9.68 ± 2.88 |

TABLE 4

The average value and standard error of CADLI score of data by gender

| Sex | Prior to administration | RXM 30-days administration | PTX 30-days administration | RXM*PTX 30-days administration | RXM*PTX 60-days administration | After the end of administration |
|---|---|---|---|---|---|---|
| Male | 35.55 ± 3.49 | 36.41 ± 3.28 | 35.41 ± 3.40 | 13.73 ± 2.82 | 8.73 ± 2.25 | 8.91 ± 2.36 |
| Castrated male | 32.80 ± 2.89 | 33.23 ± 2.97 | 32.63 ± 2.87 | 12.09 ± 2.27 | 6.09 ± 2.05 | 6.25 ± 2.12 |
| Female | 32.39 ± 2.97 | 32.71 ± 2.96 | 32.43 ± 3.13 | 11.09 ± 2.07 | 5.63 ± 1.71 | 5.86 ± 2.75 |
| Spayed female | 32.94 ± 3.03 | 33.23 ± 3.01 | 32.74 ± 2.98 | 11.89 ± 2.12 | 6.43 ± 1.91 | 6.57 ± 2.00 |

TABLE 5

The average value and standard error of CADLI score of data in each age

| Age | Prior to administration | RXM 30-days administration | PTX 30-days administration | RXM*PTX 30-days administration | RXM*PTX 60-days administration | After the end of administration |
|---|---|---|---|---|---|---|
| Under 3 years of age | 34.22 ± 4.85 | 34.72 ± 4.91 | 33.94 ± 4.74 | 10.56 ± 3.32 | 6.33 ± 2.17 | 6.56 ± 2.27 |
| 4 years-6 years of age | 32.23 ± 2.83 | 32.75 ± 2.82 | 32.38 ± 3.01 | 12.45 ± 2.16 | 5.60 ± 1.68 | 5.80 ± 1.78 |
| 7 years-9 years of age | 33.18 ± 3.59 | 33.55 ± 3.54 | 32.95 ± 3.47 | 12.31 ± 3.16 | 7.32 ± 2.57 | 7.55 ± 2.65 |
| 10 years-12 years of age | 34.75 ± 2.89 | 35.18 ± 2.89 | 34.61 ± 2.84 | 11.82 ± 2.07 | 7.53 ± 2.34 | 7.64 ± 2.42 |
| Over 13 years of age | 31.84 ± 4.01 | 32.32 ± 4.07 | 31.68 ± 3.93 | 12.58 ± 2.53 | 6.16 ± 2.75 | 6.21 ± 2.81 |

Measurement Methods for SLK Value and SQK Value

Outermost corneocytes (peeled keratinocytes) were harvested by tape stripping using the horny checker PRO type (manufactured by Promo Tool Co.) at five sites of the neck, the fossa, the back, the forearm, and the lower leg. The harvested keratinocytes were immediately stained with Diff-QuicII solution (manufactured by Sysmex Corporation) for 10 seconds, washed with water after dyeing, and photographed at a magnification of 100 with a digital camera for microscopes (Moticam 580 INT manufactured by SHIMADZU). However, unlike humans, in desquamated keratinocytes in animals, keratinocytes with two kinds of characteristic morphologies exist. One is a slender peeled off Keratinocytes (SLK) in an elongated form of peeled keratinocytes stained deep blue in Diff-QuicII solution, and the other one stained blue thinner than SLK, is peeled keratinocytes shaped like squares Square Peeled off Keratinocytes (SQK). Therefore, the following image processing was carried out in order to measure the appearance areas of these two peeling keratinocytes. First, the obtained image was processed into a monochrome paint using the GNU Image Manipulation Program (GIMP 2.8.14), and posterization was made so that SQK disappeared and only SLK could be drawn. Posterized image was processed by threshold value and the ratio of black part was measured using histogram of processed image and this measured value was taken as the appearance area (SLK value) of SLK. Next, the same image is processed into a monochrome paint again, but this time it was posterized so that all keratinocytes can be depicted. After that, processing was carried out in the same manner as described above, the proportion of the black portion was measured from the histogram, and the value obtained by subtracting the measurement value of SLK from this measurement value was taken as the appearance area (SQK value) of SQK. This measurement was performed for each case at the above five sites, and the sum of the SLK values of the five sites and the sum of the SQK values were calculated. Based on the calculated result, if the sum of the SQK values is larger than the SLK value, it is regarded as a case where SQK is more frequent.

INDUSTRIAL APPLICABILITY

The present invention can be utilized in the veterinary industry, veterinary medicine industry.

The invention claimed is:

1. A method for treating atopic dermatitis in a dog, comprising administering 3.0 mg/kg to 7.0 mg/kg of roxithromycin and 15.0 mg/kg to 35.0 mg/kg of pentoxifylline in combination.

2. The method for treating atopic dermatitis according to claim 1, characterized by administrating the roxithromycin and the pentoxifylline at the same time with meals every 12 hours for 60 days.

3. A method for treating atopic dermatitis in a dog, characterized by administrating 3.0 mg/kg to 7.0 mg/kg of roxithromycin and/or a pharmaceutically acceptable salt thereof and 15.0 mg/kg to 35.0 mg/kg of pentoxifylline and/or a pharmaceutically acceptable salt thereof in combination.

4. The method for treating atopic dermatitis according to claim 3, characterized by administrating the roxithromycin and/or pharmaceutically acceptable salt thereof, and the pentoxifylline and/or pharmaceutically acceptable salt thereof together with meals at the same time for 60 days every 12 hours.

* * * * *